(12) United States Patent
Odell et al.

(10) Patent No.: US 6,503,230 B2
(45) Date of Patent: Jan. 7, 2003

(54) NEEDLE SHIELD FOR A PREFILLABLE SYRINGE

(76) Inventors: Robert B. Odell, 357 Pulis Ave., Franklin Lakes, NJ (US) 07417; Sandor Gyure, 56 Nestro Rd., West Orange, NJ (US) 07052

( * ) Notice: Subject to any disclaimer, the term of this patent is extended or adjusted under 35 U.S.C. 154(b) by 0 days.

(21) Appl. No.: 09/920,528

(22) Filed: Aug. 1, 2001

(65) Prior Publication Data

US 2001/0044608 A1 Nov. 22, 2001

Related U.S. Application Data

(63) Continuation of application No. 08/127,524, filed on Jul. 31, 1998, now abandoned.

(51) Int. Cl.[7] .............................. A61M 5/00; A61M 5/32
(52) U.S. Cl. ...................... 604/263; 604/192; 604/199
(58) Field of Search ................................ 604/263, 218, 604/192, 197, 198, 162, 164.08, 171, 193, 199; 206/364, 365; 215/307; 433/89–90; 222/551, 562

(56) References Cited

U.S. PATENT DOCUMENTS

| 2,219,301 A | 10/1940 | Erhard |
| 2,400,722 A | 5/1946 | Swan |
| 2,688,963 A | 9/1954 | Smith |
| 2,857,912 A | 10/1958 | Feinstone et al. |
| 2,972,991 A | 2/1961 | Burke |
| 3,073,307 A | 1/1963 | Stevens |
| 3,112,747 A | 12/1963 | Cowley |
| 3,306,291 A | 2/1967 | Burke |
| 3,380,448 A | 4/1968 | Sadove et al. |
| 3,381,686 A | 5/1968 | Pierce |
| 3,381,813 A * | 5/1968 | Coanda et al. ............... 206/365 |
| 3,390,759 A | 7/1968 | Vanderbeck |
| 3,637,072 A | 1/1972 | Narusawa et al. |
| 3,865,236 A | 2/1975 | Rycroft |
| 3,889,673 A | 6/1975 | Dovey et al. |
| 4,085,737 A | 4/1978 | Bordow |
| 4,215,087 A | 7/1980 | Mathison |
| 4,240,425 A | 12/1980 | Akhavi |
| 4,248,246 A | 2/1981 | Ikeda |
| 4,468,223 A | 8/1984 | Minagawa et al. |
| 4,474,734 A | 10/1984 | Cooper |
| 4,507,118 A | 3/1985 | Dent |
| 4,728,321 A | 3/1988 | Chen |
| 4,735,311 A | 4/1988 | Lowe et al. |
| 4,964,866 A | 10/1990 | Szwarc ........................ 604/192 |
| 4,986,818 A | 1/1991 | Imbert et al. ................ 604/192 |
| D322,671 S | 12/1991 | Szwarc |
| 5,085,647 A | 2/1992 | Henderson et al. |
| D332,308 S | 1/1993 | Imbert et al. |
| 5,259,840 A | 11/1993 | Boris |
| 5,308,330 A | 5/1994 | Grimard ...................... 604/110 |
| 5,529,189 A | 6/1996 | Feldschuh |
| 5,607,400 A | 3/1997 | Thibault et al. ............. 604/230 |
| 5,613,615 A * | 3/1997 | Zeyfang et al. ............. 137/843 |
| 5,980,495 A | 11/1999 | Heinz et al. |

FOREIGN PATENT DOCUMENTS

| EP | 0 229 204 A1 | 7/1987 |
| EP | 0 976 415 A2 | 2/2000 |
| FR | 2 644 069 | 9/1990 |
| GB | 981009 | 1/1965 |

* cited by examiner

*Primary Examiner*—Brian L. Casler
*Assistant Examiner*—Catherine Serke
(74) *Attorney, Agent, or Firm*—Howard & Howard

(57) ABSTRACT

A syringe assembly includes a needle sheath that has a cavity that receives a needle cannula. The needle sheath can be formed of materials such as thermoplastic elastomers or plastics yet still be utilized with conventional gas sterilizing processes. The needle sheath includes a passage that permits the sterilizing gases to enter the cavity while preventing entry of microorganisms into the cavity. Thus, a syringe assembly is provided that facilitates sterilizing a needle after the needle sheath has been placed over the needle.

12 Claims, 7 Drawing Sheets

NEEDLE SHIELD FOR A PREFILLABLE SYRINGE

This is a continuation of Ser. No. 08/127,524 filed Jul. 31, 1998 now abandoned.

BACKGROUND OF THE INVENTION

This invention generally relates to a syringe assembly having a needle sheath.

Increasingly, medicaments are supplied from manufacturers in prefilled syringe assemblies. Such assemblies include a syringe that has a needle cannula and is filled with the medicament. Typically, a needle sheath covers the needle cannula to prevent accidental contact with the needle. Manufacturers supply such syringe assemblies as prepackaged, sterile, single use units. Thus, it is necessary to create a syringe assembly than can be sterilized after the needle sheath is placed over the needle cannula.

In the past, needle sheaths were primarily composed of rubber. With the advent of modern thermoplastic elastomers, many manufacturers have switched to thermoplastic elastomers as the material of choice for needle sheaths. Thermoplastic elastomers offer the advantages of being: cleaner than natural rubber products; providing better dimensional control of parts; available in a wider variety of synthetic materials to insure compatibility with a particular medicament; lower cost than natural rubber; and reduced leeching of materials from the needle sheath into the medicament.

Thermoplastic elastomers also permit a wider choice of sterilization methods between gases like ethylene oxide, irradiation, or autoclaving. One problem with some synthetic thermoplastic elastomers is that the particular composition which is most compatible with a particular medicament has a low permeability to a sterilizing gas.

Thus, it is desirable to provide a needle sheath that can be sterilized using any sterilizing gas while permitting the needle sheath to be composed of any thermoplastic elastomer, including one having a low permeability to the particular sterilizing gas. In addition, it is sometimes desirable to produce a needle sheath formed of plastic. Plastics generally have low gas permneability. Thus, it is desirable to provide a needle sheath that can be formed of materials with low gas permeability and still be sterilized by a sterilizing gas.

SUMMARY OF THE INVENTION

In general terms, this invention provides a syringe assembly having a needle sheath that can be formed of a material having a low gas permeability, but which can be sterilized using a sterilizing gas.

A syringe assembly designed according to this invention includes a syringe body, a needle cannula, and a needle sheath. The needle sheath has a body portion with a cavity that is open at a first end and closed at a second end opposite the first end. The cavity receives the needle cannula and includes a passage in communication with the first end of the cavity. The passage has a shape that permits gas from the external atmosphere to flow into the cavity while simultaneously preventing entry of microorganisms from the external atmosphere into the cavity.

These and other features and advantages of this invention will become more apparent to those skilled in the art from the following detailed description of the presently preferred embodiment. The drawings that accompany the detailed description can be described as follows.

DETAILED DESCRIPTION OF THE PREFERRED EMBODIMENT

Figure 1:
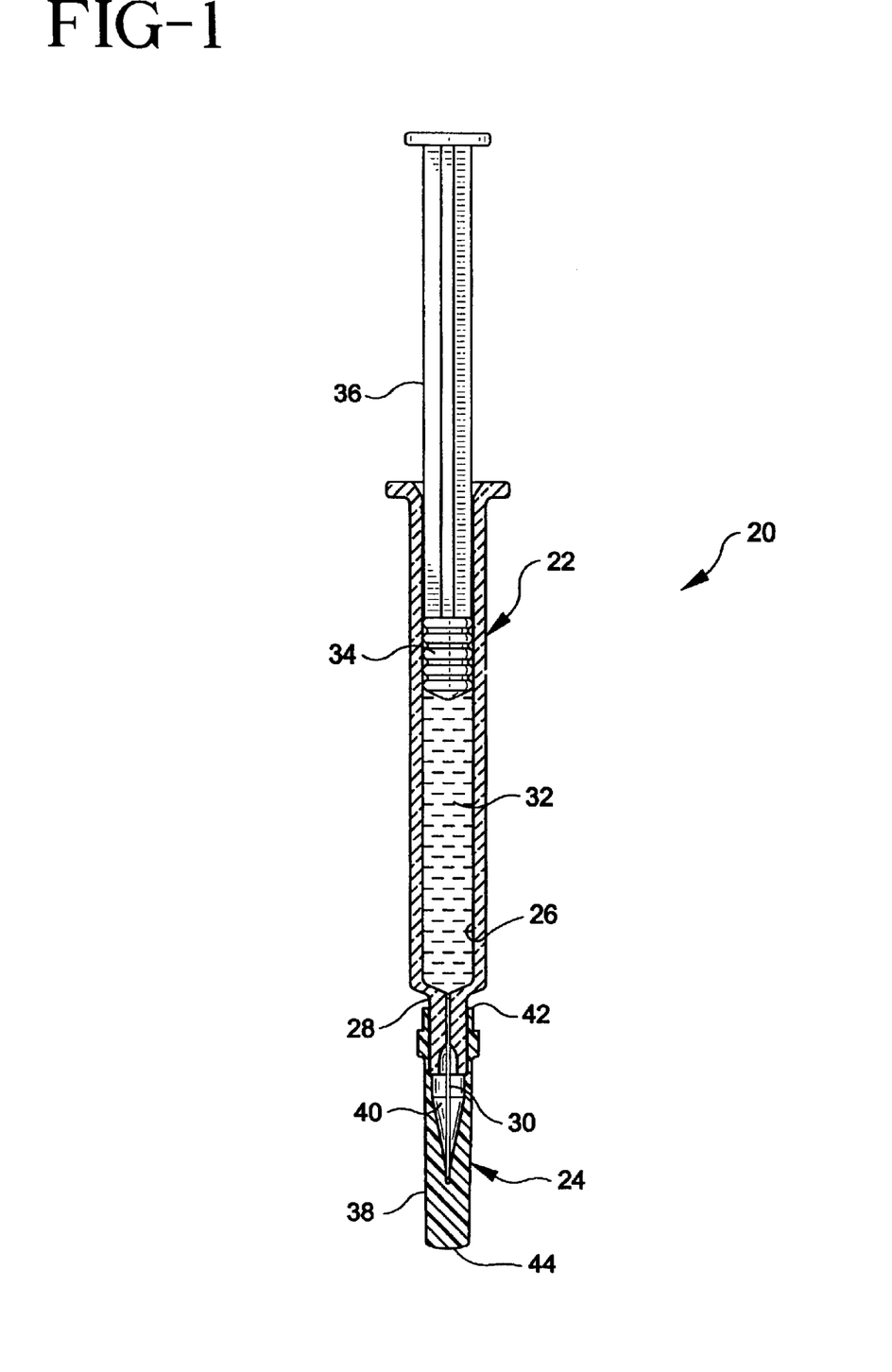
FIG. 1 is a cross-sectional view of a syringe assembly designed according to the present invention.

A syringe assembly is generally indicated at 20 in FIG. 1. The syringe assembly 20 includes a syringe body 22 and a needle sheath 24. The syringe body 22 has an interior chamber 26 that receives a medicament 32 and is in communication with a passage in a neck portion 28. An integral needle cannula 30 is supported on the neck portion 28 and in communication with the interior chamber 26 through the passage in the neck portion 28. A conventional stopper 34 and plunger rod 36 are used to eject the medicament 32 from the needle cannula 30 while administering an injection in a conventional manner.

The needle sheath 24 includes a body portion 38 with a cavity 40. The needle sheath 24 has a first end 42 and a second end 44. The first end 42 defines the cavity opening and is received over the neck portion 28. In FIG. 1, the syringe assembly 20 is shown as prefilled syringe containing the medicament 32 loaded in the interior chamber 26. Of course, the syringe assembly 20 could be packaged without any medicament 32 in the interior chamber 26.

Figure 2:
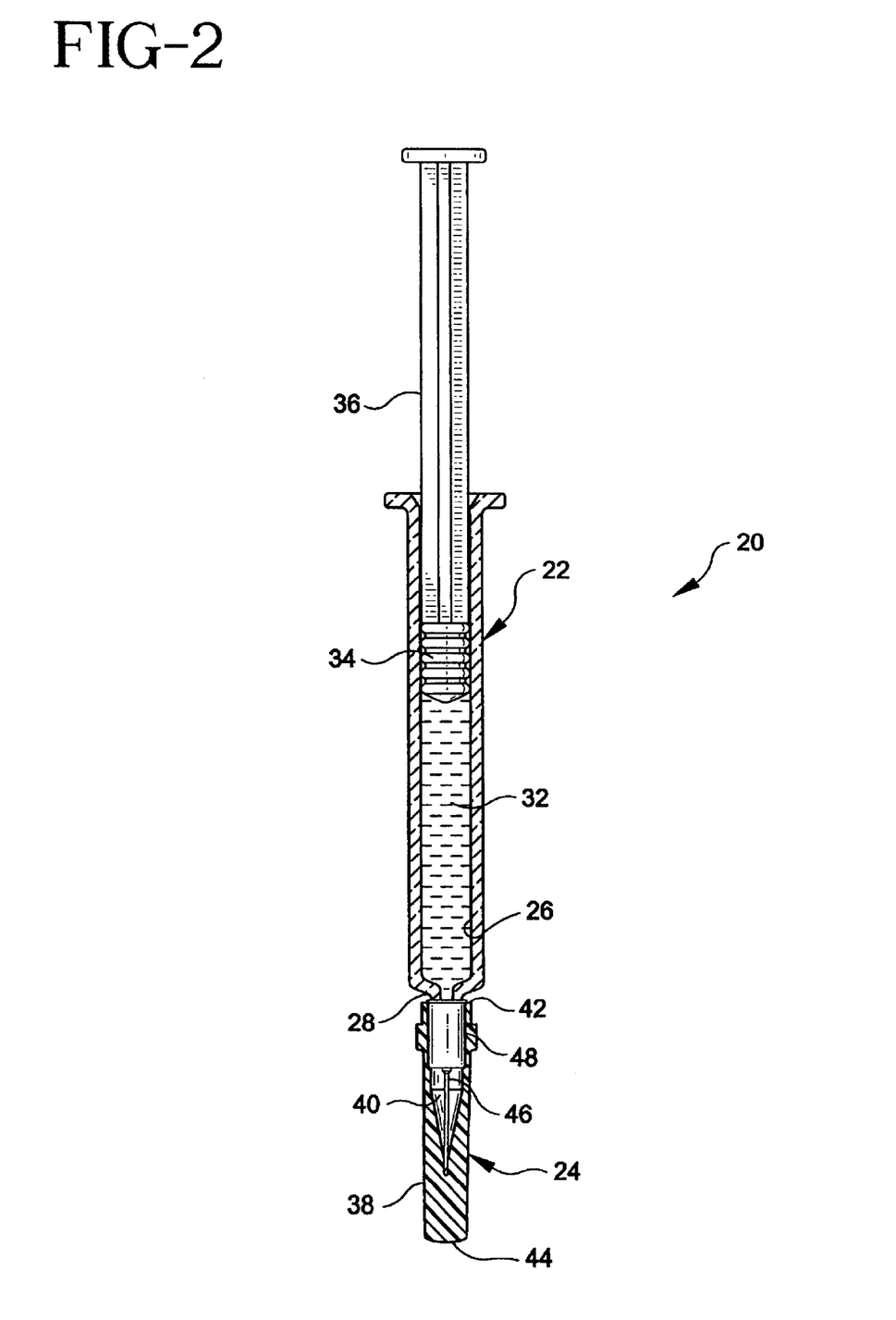
FIG. 2 is a cross-sectional view of another embodiment of a syringe assembly designed according to the present invention.

FIG. 2 illustrates another syringe assembly 20 designed according to the present invention. The syringe assembly in FIG. 2 does not include an integral needle cannula 30, but includes a needle cannula 46 extending from a hub 48. The hub 48 and needle cannula 46 are supported on the neck portion 28 of the syringe body 22.

Figure 3:
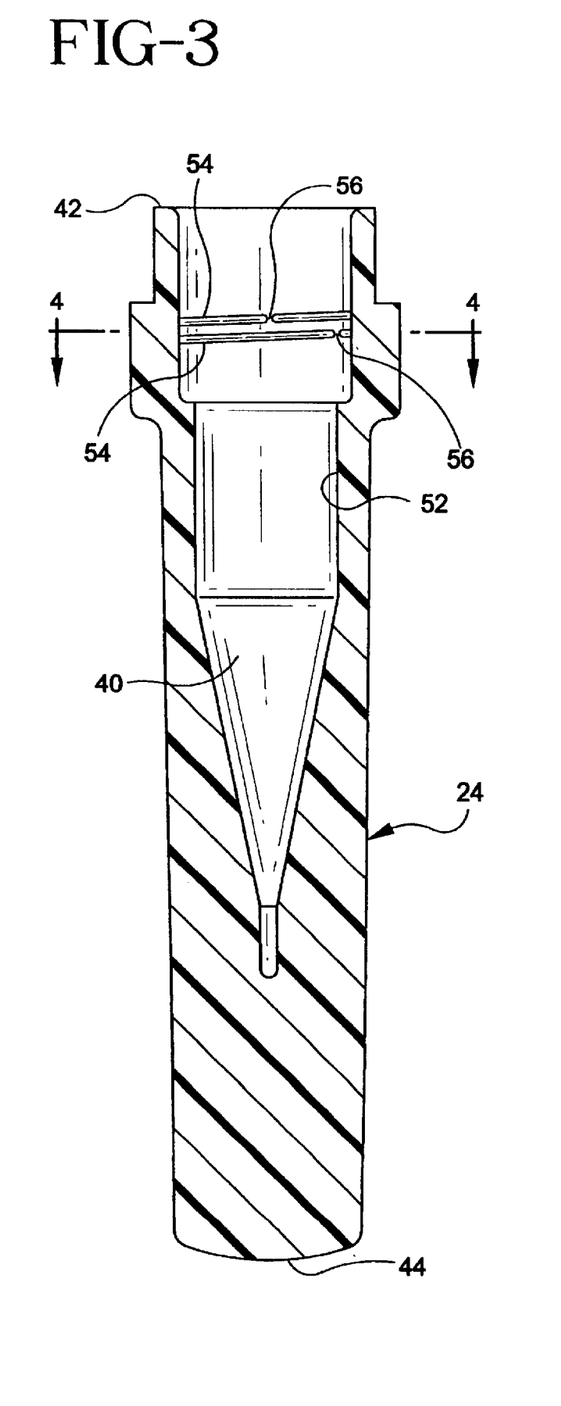
FIG. 3 is a cross-sectional side view of a needle sheath designed according to the present invention.
Figure 4:
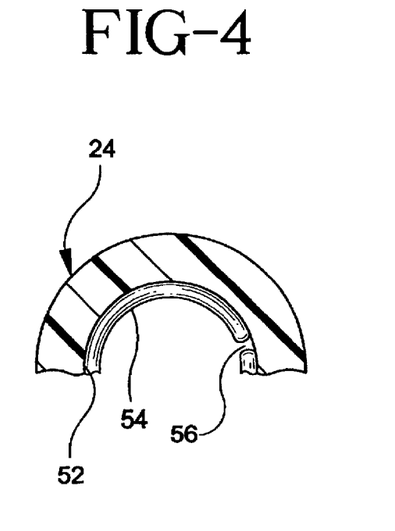
FIG. 4 is a cross-sectional view along line 4—4 of FIG. 3.

A cross-sectional side view of a needle sheath 24 designed according to one embodiment of the present invention is shown in FIGS. 3 and 4. The cavity 40 has an inner surface 52. Ridges 54 are located on the inner surface 52 of the cavity 40. Each ridge 54 includes a gap 56. Preferably, the gap 56 has a cross-sectional size that is between about 0.00001 and 0.00008 square inches. The gap 56 of adjacent ridges 54 are circumferentially offset from each other. The amount of offset between gaps 56 may be varied as needed in a particular situation. In one example, only a single ridge 54 is used.

When the needle sheath 24 is fit over the neck portion 28, the ridges 54 sealingly engage the outer surface of the neck portion 28, for example. The gap 56 provides a passage between the first end 42 and the cavity 40. The size of the gap 56 permits sterilizing gas from outside of the cavity 40 to flow into the cavity 40 while simultaneously preventing undesirable microorganisms from entering the cavity 40.

The design of this invention permits a syringe assembly 20 to be assembled under non-sterile conditions and to subsequently be sterilized by a sterilizing gas such as ethylene oxide while using thermoplastic elastomers to form the needle sheath 24. The gaps 56 permit the sterilizing gas to flow into the cavity 40 and to sterilize the interior of the cavity 40 and either the integral needle cannula 30 or the needle cannula 46.

Figure 5:
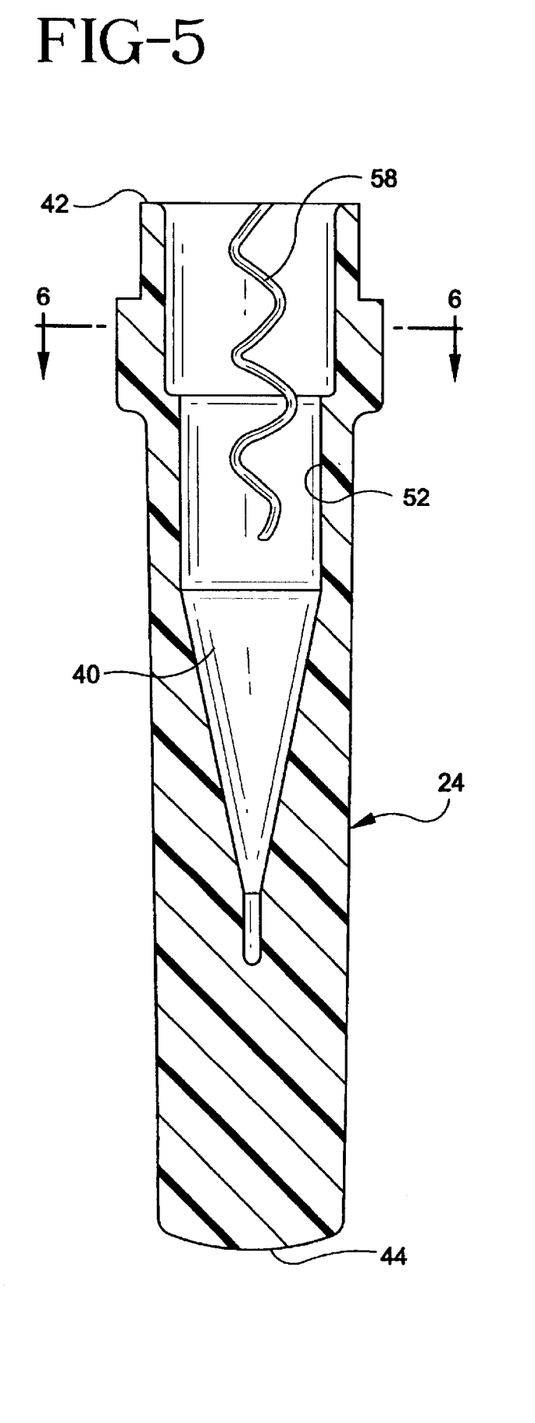
FIG. 5 is a cross-sectional side view of another embodiment of a needle sheath designed according to the present invention.
Figure 6:
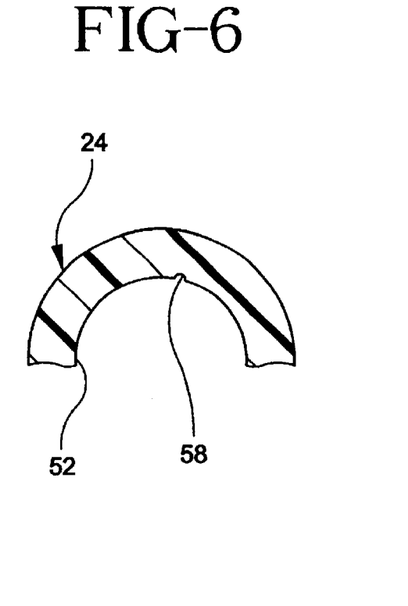
FIG. 6 is a cross-sectional view along line 6—6 of FIG. 5.

FIGS. 5 and 6 illustrate an alternative embodiment of a needle sheath 24 designed according to the present invention. The needle sheath 24 includes a groove 58 formed on the inner surface 52 of the cavity 40. The groove 58 has a shape that provides a non-linear pathway from the first end 42 into the cavity 40. The nonlinear pathway provided by the groove 58 permits a sterilizing gas to enter the cavity 40 while simultaneously preventing undesirable microorganisms from entering the cavity 40. The groove 58 must extend into the cavity 40 sufficient to allow the sterilizing gas to contact the needle.

Figure 7:
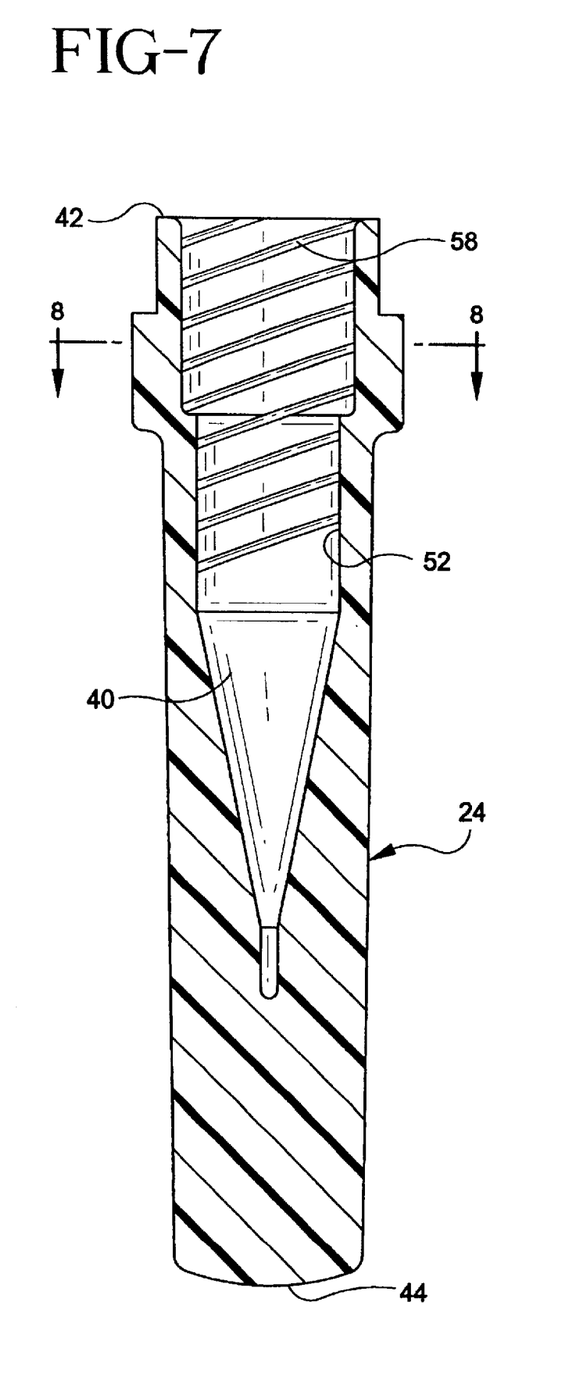
FIG. 7 is a cross-sectional side view of another embodiment of a needle sheath designed according to the present invention.
Figure 8:
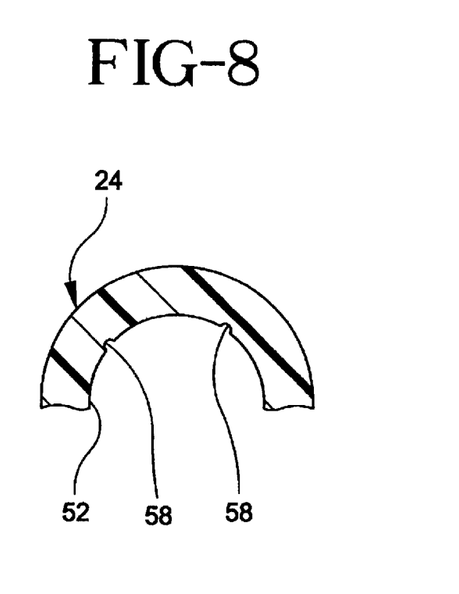
FIG. 8 is a cross-sectional view along line 8—8 of FIG. 7.

As shown in FIGS. 7 and 8, a groove 58' could provide a pathway that spirals around the inner surface 52 of the cavity 40. In the embodiments shown in FIGS. 5–8 the inner surface 52 of the needle sheath 24 will be in sealing engagement with either the neck portion 28 or the hub 48 when the syringe assembly 20 is complete. The groove 58 and 58', however, allows for the sterilizing gas to enter the cavity 40 during a sterilizing process.

Figure 9:
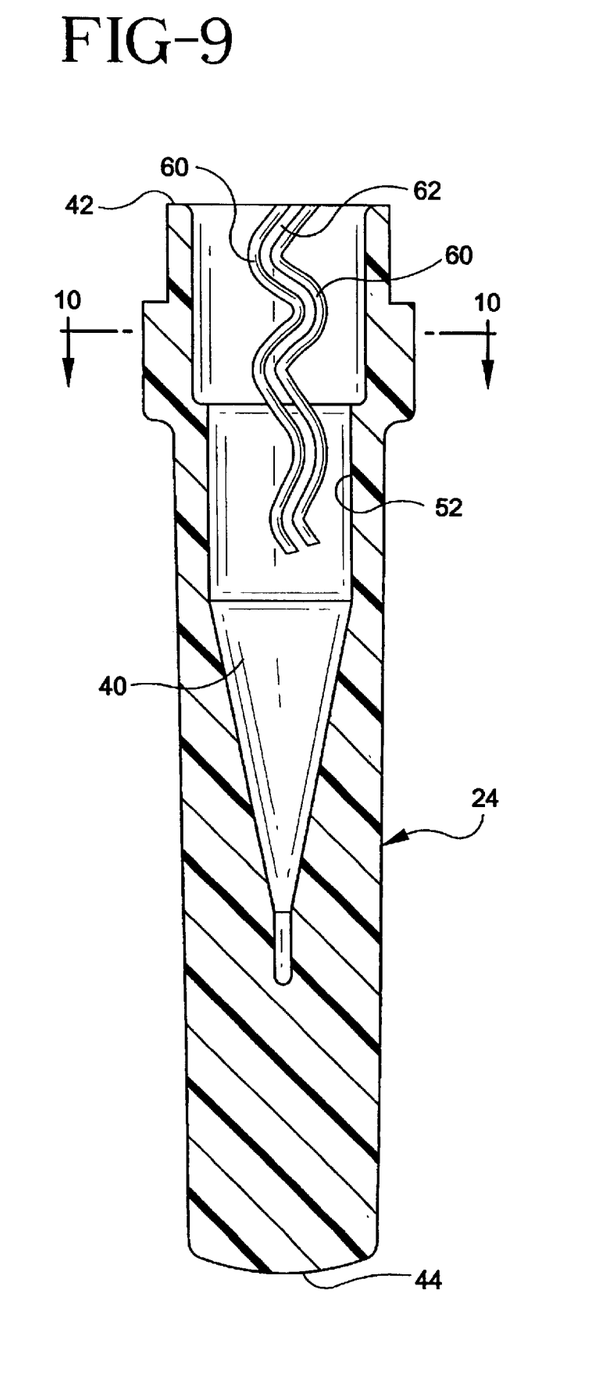
FIG. 9 is a cross-sectional side view of another embodiment of a needle sheath designed according to the present invention.
Figure 10:
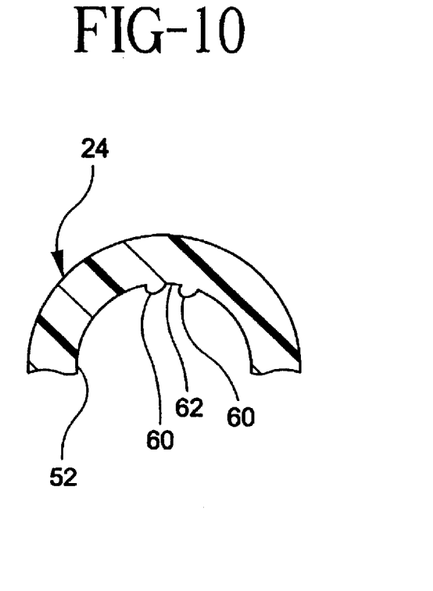
FIG. 10 is a cross-sectional view along line 10—10 of FIG. 9.
Figure 11:
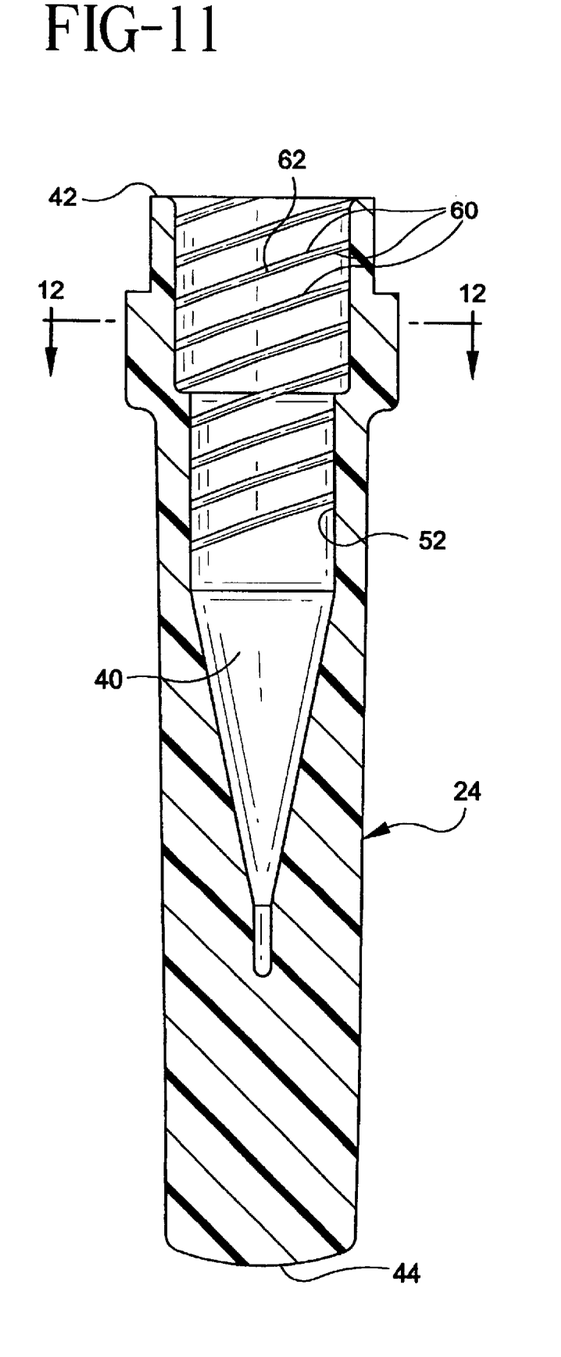
FIG. 11 is a cross-sectional side view of another example of a needle sheath designed according to the present invention.
Figure 12:
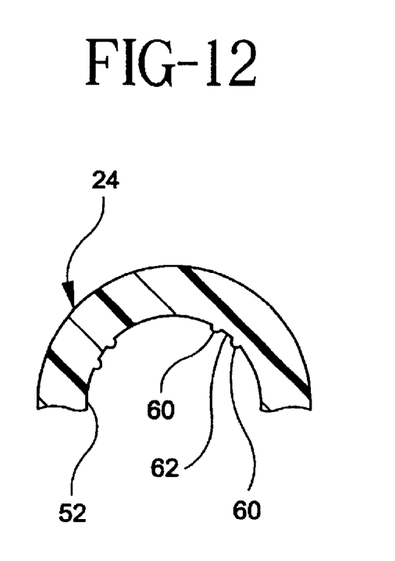
FIG. 12 is a cross-sectional view along line 12—12 of FIG. 11.

An alternative embodiment of the needle sheath 24 is shown in FIGS. 9 through 12. In FIG. 9, a plurality of ridges 60 are formed on the inner surface 52 of the cavity 40. A gap 62 is located between the plurality of ridges 60. The gap 62 provides a passage from the first end 42 into the cavity 40. The gap 62 permits sterilizing gases to enter the cavity 40 while preventing undesirable microorganisms in the external atmosphere from entering the cavity 40. In the embodiment shown in FIGS. 9 and 10, the ridges 60 and the majority of the inner surface 52 will be in sealing engagement with either the neck portion 28 or the hub 48 when the syringe assembly 20 is fully assembled. As shown in FIGS. 11 and 12, the ridges 60 have a shape that provides a spiralling gap 62 around the inner surface 52 of the cavity 40.

The shape of the passage permitting sterilizing gas to enter the cavity 40 may take a variety of forms. It is imperative that the passage have some contour or non-linearity so that microorganisms cannot find their way into the cavity 40. Otherwise, sterility would not be preserved. The example passages disclosed in this description provide the necessary two-fold function of allowing gas flow while simultaneously preventing microorganism entry.

The needle sheath 24 can be formed from rubber, thermoplastic elastomers, or plastics. The particular material used to form the needle sheath 24 is selected based on compatibility with the medicament 32 that is eventually loaded into the syringe assembly 20 and other design considerations.

The foregoing description is exemplary rather than limiting in nature. Variations and modifications to the disclosed embodiment may become apparent to those skilled in the art and do come within the scope of this invention. Accordingly, the scope of legal protection afforded this invention can only be determined by studying the following claims.

We claim:

1. A syringe assembly comprising:
   a tubular syringe barrel;
   a needle hub extending from said tubular syringe barrel having a diameter less than said tubular syringe barrel;
   a needle cannula supported by said needle hub; and
   a needle sheath formed of a thermoplastic elastomer having a low permeability to a sterilizing gas including an open end and a closed end, a first cylindrical cavity opening through said open end of said needle sheath having a cylindrical internal surface including an internal diameter generally equal to an external diameter of said needle hub receiving said needle hub in sealed relation and a second cavity contiguous with said first cavity having an internal surface including an internal diameter less than said internal diameter of said first cavity, and a continuous curvilinear groove or rib on said internal surface of said first cavity extending into said second cavity defining a passage and extending from said open end of said needle sheath into said second cavity dimensioned to permit sterilizing gas from an external atmosphere to flow into said second cavity through said open end to sterilize said needle hub and needle cannula and preventing entry of microorganisms from the external atmosphere into said cavities.

2. The syringe assembly as defined in claim 1, wherein said continuous curvilinear groove or rib is a spiral groove or rib.

3. The syringe assembly as defined in claim 1, wherein said continuous curvilinear groove or rib comprises a continuous spiral groove extending from said open end of said needle shield through said internal surface of said first cavity into said internal surface of said second cavity.

4. The syringe assembly as defined in claim 3, wherein said internal surface of said first and second cavities includes at least two spaced continuous spiral grooves.

5. The syringe assembly as defined in claim 1, wherein said groove or rib is a continuous non-spiral irregular curvilinear groove extending from said open end of said needle shield through said internal surface of said first cavity into said internal surface of said second cavity.

6. The syringe assembly as defined in claim 1, wherein said continues curvilinear groove or rib has a cross-sectional size of between 0.00001 and 0.00008 square inches.

7. A syringe assembly, comprising:
   a tubular syringe barrel having an open end, a reduced diameter neck portion and a hub having a diameter less than said tubular syringe barrel and a needle cannula supported by said needle hub; and
   a needle sheath formed of a polymer having a low gas permeability to a sterilizing gas including a first open end and a closed end, a first cylindrical cavity opening through said first open end having a cylindrical internal surface, a second cylindrical cavity contiguous with said first cylindrical cavity including a cylindrical internal surface having a diameter less than said first cylindrical cavity and a third cavity contiguous with said second cylindrical cavity having an internal diameter less than said second internal cavity receiving said needle cannula, a continuous curvilinear groove or rib extending from said first open end through said first cylindrical internal surface of said first cavity into said cylindrical internal surface of said second cavity permitting sterilizing gas from an external atmosphere to flow into and out of said second cylindrical cavity while preventing entry of microorganisms, and said internal diameters of said first and second cavities having a diameter generally equal to said reduced diameter neck portion or said hub to sealingly engage one of said neck portion and said hub.

8. The syringe assembly as defined in claim 7, wherein said third cavity includes a generally conical internal surface having a minor diameter generally equal to the diameter of said needle cannula.

9. The syringe assembly as defined in claim 7, wherein said continuous curvilinear groove or rib is a continuous spiral groove.

10. The syringe assembly as defined in claim 7, wherein said internal surfaces of said first and second cylindrical cavities includes at least two spaced continuous spiral grooves.

11. The syringe assembly as defined in claim 7, wherein said continuous curvilinear groove or rib is a continuous non-spiral irregular curvilinear groove.

12. The syringe assembly as defined in claim 7, wherein said continuous curvilinear groove or rib has a cross-sectional area of between 0.00001 and 0.00008 square inches.

* * * * *

UNITED STATES PATENT AND TRADEMARK OFFICE
CERTIFICATE OF CORRECTION

PATENT NO.   : 6,503,230 B2
DATED        : January 7, 2003
INVENTOR(S)  : Odell et al.

It is certified that error appears in the above-identified patent and that said Letters Patent is hereby corrected as shown below:

<u>Title page,</u>
Item [63], Related U.S. Application Data, should read:

-- [63] Continuation of application No. 09/127,524, filed on Jul. 31, 1998, now abandoned. --

Signed and Sealed this

Twenty-ninth Day of July, 2003

JAMES E. ROGAN
*Director of the United States Patent and Trademark Office*